United States Patent [19]
Fogel

[11] Patent Number: 5,840,285
[45] Date of Patent: Nov. 24, 1998

[54] DERMATOLOGICAL COMPOSITIONS USING A SERIES OF UNUSUALLY SAFE ESTERS AS COSMETIC EMOLLIENTS WITH UNIQUE AND IDEAL PHYSICAL PROPERTIES

[75] Inventor: Arnold W. Fogel, Upper Saddle River, N.J.

[73] Assignee: Bernel Chemical Co., Inc, Englewood, N.J.

[21] Appl. No.: 154,562

[22] Filed: Nov. 19, 1993

Related U.S. Application Data

[63] Continuation-in-part of Ser. No. 806,927, Dec. 11, 1991, abandoned.

[51] Int. Cl.⁶ .................................................. A61K 7/025
[52] U.S. Cl. ............................. 424/64; 424/63; 514/547; 514/785; 514/873
[58] Field of Search ..................................... 514/547, 785, 514/873; 424/64, 63

[56] References Cited

U.S. PATENT DOCUMENTS

| | | | |
|---|---|---|---|
| 1,815,878 | 7/1931 | Van Schaack | 560/190 |
| 1,993,736 | 3/1935 | Graves et al. | 560/190 X |
| 1,993,738 | 3/1935 | Graves et al. | 560/190 X |
| 2,218,181 | 10/1940 | Searle et al. | 560/190 X |
| 2,333,666 | 11/1943 | Moore et al. | 560/190 X |
| 2,509,203 | 5/1950 | Bartlett | 560/190 |
| 2,721,877 | 10/1955 | Popkin et al. | 560/190 |
| 3,862,147 | 1/1975 | Cooley et al. | 560/190 X |
| 3,905,943 | 9/1975 | Gormley | 560/190 X |
| 4,956,492 | 9/1990 | Dekraker et al. | 560/190 |

OTHER PUBLICATIONS

Chem Abstracts 113:178040c, plus Cas online printout, Amaya et al, 1990.

*Primary Examiner*—Samuel Barts
*Attorney, Agent, or Firm*—Henry D. Coleman; R. Neil Sudol

[57] ABSTRACT

This invention introduces a series of esters to be used as emollients in cosmetic formulations. These are $C_{12}$–$C_{15}$ blended alcohol esters, $C_{16}$, $C_{18}$, $C_{20}$ and $C_{20}$ alcohol esters of fumaric and maleic acids.

When used "neat" or in formulations they are unusually safe by standard cosmetic tests. A unique and ideal physical property of the $C_{12}$–$C_{15}$ blend alcohol ester of fumaric acid is that it is a solid melting at body temperature.

These esters, with their safety and physical properties, introduce the cosmetic chemist to new ideal cosmetic emollients for use in any cosmetic formulation.

10 Claims, No Drawings

DERMATOLOGICAL COMPOSITIONS USING A SERIES OF UNUSUALLY SAFE ESTERS AS COSMETIC EMOLLIENTS WITH UNIQUE AND IDEAL PHYSICAL PROPERTIES

This is a continuation in part of application Ser. No. 07/806,927 filed Dec. 11, 1991, now abandoned.

BACKGROUND OF THE INVENTION

1. Field of the Invention

Great emphasis is placed on safety, for obvious reasons, on products and raw materials used in cosmetic formulations.

The present invention relates to a series of esters that introduce cosmetic emollients which are unusually safe by all standard testing, even when tested "neat". It is not normal for almost all cosmetic esters to give "0" readings when tested "neat" on safety tests. The esters introduced all give "0" readings "neat", an indication of unusually safe products.

Beyond the safety aspects, this invention introduces cosmetic emollients which are unusually stable. The $C_{12}$–$C_{15}$ alcohol blend esters of fumaric acid introduces one of the long sought ideal physical properties in a cosmetic ester, that is, a solid which melts at body temperature, teaching the use of di-isocetyl fumarate as an emollient. There are no closely related diesters used as cosmetic emollients. The present invention is patentably distinguished over the state of the present art.

2. Description of the Prior Art a) U.S. Pat. No. 4,851,439 uses a fumaric acid derivative as an active ingredient in a pharmaceutical composition. One carboxylic group of the fumaric acid is esterified with a long chain fatty alcohol and the other carboxylic group is either in the free acid form or esterified with a lower aliphatic alcohol. These esters are described as "pro-drugs" and no emollient activity is attributed to them.

b) U.S. Pat. No. 3,976,789 discloses a cosmetic composition having a tri or tetraester emollient therein. The ester is made by esterifying a polyol having three or four hydroxy groups with a carboxylic acid selected from the group consisting of a 2-ethyl-hexanoic acid, 2-hexyl-decanonic acid and 2-heptyl-undecanoid acid.

c) U.S. Pat. No. 4,030,991 discloses an emollient containing an ester made by esterifying cis-6-hexadecanoic acid with certain alcohol or polyol compounds (glycerol, ethylene, glycol, propylene glycol and straight or branched chain monohydric alcohols).

d) U.S. Pat. No. 4,766,153 discloses certain alkyl polyoxyalkylene carboxylate esters which are said to be useful as emollients in skin care compositions.

e) U.S. Pat. No. 4,009,256 disclosed a shampoo composition which may contain an ester as an emollient.

f) U.S. Pat. No. 4,311,709 disclosed an antibiotic which is in the form of a fumarate salt.

g) U.S. Pat. No. 2,218,181 describes certain dialkyl esters of unsaturated acids as insecticides.

h) U.S. Pat. No. 2,333,666 introduces other dialkyl esters of unsaturated dicarboxylic acids as insecticides.

i) U.S. Pat. No. 2,509,203 relates to novel chemical products made by the polymerization of lauryl fumarate.

j) U.S. Pat. No. 4,956,492 introduces dialkyl fumarate vinyl acetate copolymers useful as dewaxing aids.

k) U.S. Pat. No. 1,993,738 introduces esters of myristyl alcohol and still more particularly to the polycarboxylic acid esters of myristyl alcohol.

l) U.S. Pat. No. 2,721,877 uses fumaric and nucleic acid esters as lubricating oil additives and a process for their preparation.

m) U.S. Pat. No. 3,862,147 introduces the maleic anhydride process utilizing monohydric alcohols as a dehydration or entraining agent.

n) U.S. Pat. No. 1,815,878 relates to esters of secondary alcohols containing more than 6 carbon atoms to the molecule with dibasic organic acids.

o) U.S. Pat. No. 1,993,736 shows new organic acid esters and their preparation specifically polybasic carboxylic acid esters containing an esterified higher alkyl group.

p) U.S. Pat. No. 3,905,943 deals with the preparation of fumarates.

OBJECT AND SUMMARY OF THE INVENTION

It is the object of this invention to introduce a series of esters which are to be used as cosmetic emollients in cosmetic formulations. These esters are characterized by unusual safety, even when tested "neat", that is, 100% pure ester. It should be noted that although these esters appear in the prior art nowhere have they ever been introduced as cosmetic emollients.

It is not normal for almost all cosmetic esters to give "0" readings in standard testing. The three standard tests used are the Draize Dermal Test, the Draize Occular Test and Federal Hazard and Safety Act Test, requiring oral feeding of 5 g/Kg (animal testing).

The esters introduced here all give "0" readings on testing, a totally unusual and unique property for cosmetic esters.

It is the further object of this invention to introduce to the cosmetic chemist an ester which has ideal physical properties and safety which melts at body temperature. The $C_1$–$C_{15}$ blended alcohol fumarate, one of the esters introduced is a solid which melts at body temperature.

The esters have the following properties which make them the ideal cosmetic emollients to date to anyone knowledgeable and skilled in the art:

1. Unique and unusual safety (Zero Safety Scores).
2. Unique and unusual physical properties, (melting point, freezing point).
3. Unique and unusual viscosity (thicker than expected).
4. Unique and unusual emolliency.
5. Anti-tack properties (plasticizers for sticky raw materials).
6. Melting point adjuster—used to adjust the melting point of a solid, gel or emulsion product.
7. Freezing point adjuster. May be used to adjust and improve the freeze-thaw properties of an emulsion to maintain a homogeneity of physical properties and shelf stability in a required range of temperatures.
8. Pigment wetters for insoluble pigments.
9. Solubilizers for powder and crystals (solids into oils).

These unique properties are the focal point of the invention. The foregoing properties make them the esters of choice as emollients for cosmetic formulations by the cosmetic chemists. These are unique esters never introduced for use in the field of cosmetic formulations.

DETAILED DESCRIPTION OF THE INVENTION

Fumaric Acid, trans-1,2-ethylene dicarboxylic acid, and maleic acid, cis-1,2-ethylenedicarboxylic acid, react with various alcohols to produce diesters and water.

The present invention introduces a range of diesters based on alcohol moieties from $C_{12}$–$C_{26}$.

The ($C_{12}$–$C_{15}$) alcohols blend and $C_{22}$ (behenyl) alcohol fumarates and maleates have straight chain alcohol moieties. The $C_{16}$, $C_{18}$, $C_{20}$ and $C_{26}$ alcohol moieties of the esters are branched chain iso-alkyl groups.

Examples follow:

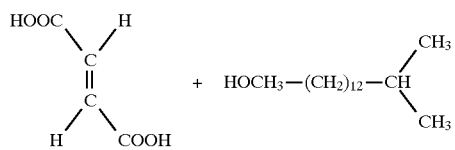

Fumaric Acid    Isocetyl Alcohol
I               II

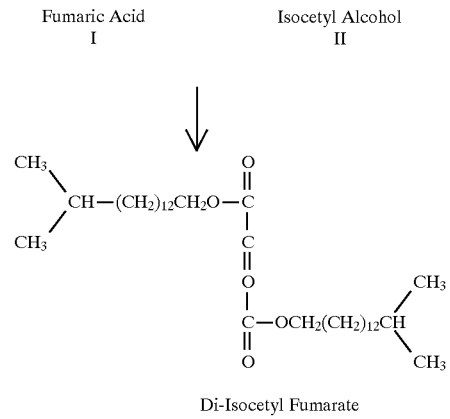

Di-Isocetyl Fumarate
III

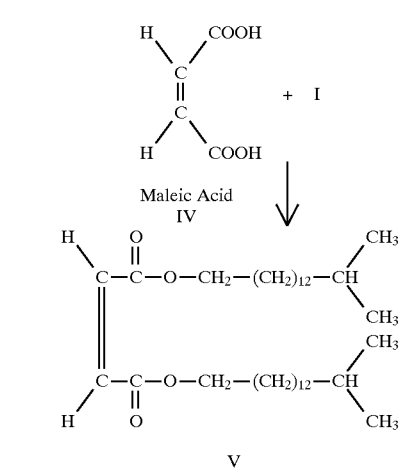

Other embodiments of the invention are formed as follows:

VI

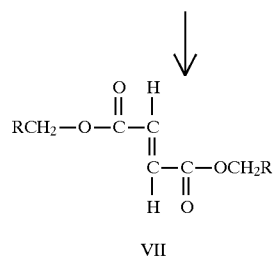

VII

-continued

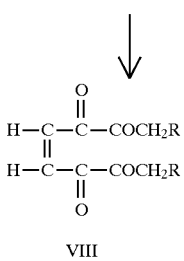

VIII

Where R is a blend of ($C_{11}$–$C_{14}$) straight chain alkyl groups with the specifications as attached for Neodol 25, the actual blend used.

The foregoing esters introduce the following properties which make them unique and unusual for use in cosmetic formulations. The 100.00% pure esters have the following properties:

Unique and unusual safety, physical properties, viscosity and emolliency properties.

Further, the anti-tack properties, melting point and freezing point adjusting properties, pigment wetting properties and their solubilizer properties make these esters ideal for use by anyone skilled and knowledgeable in cosmetic formulations.

The unexpected zero scores on the Standard Safety Tests (Draize Dermal, Draize Occular and FHSA Feeding Tests) make these esters stand out without peer in the industry. These zero scores are obtained for the "neat" product, that is, 100% ester.

It is normal for almost all cosmetic esters not to give the "zero" safety scores.

PRODUCT—NEODOL 25

| PROPERTY | UNIT OF MEASURE | ANALYSIS |
| --- | --- | --- |
| COLOR, PI-CO |  | 5 |
| WATER CONTENT, % W | % WT | 0.02 |
| HYDROXYL NUMBER |  | 273 |
| MOLECULAR WEIGHT |  | 204 |
| IODINE NO. G/100 G | G/100 G | 0.1 |
| ACID VALUE, EQ/100 G | E/100 G | 0.0029 |
| HYDROCARBON, % W | % WT | 0.09 |
| CARBONYL, PPM, C = O | PPM | 49 |

PREFERRED EMBODIMENTS OF THE INVENTION

The four preferred embodiments of the invention have the following structures:

A.

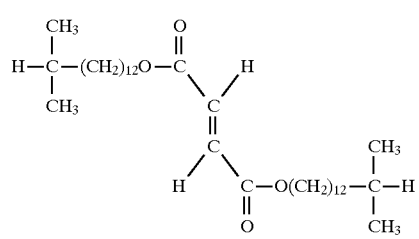

III

-continued

B.

Di-isocetyl Fumarate.

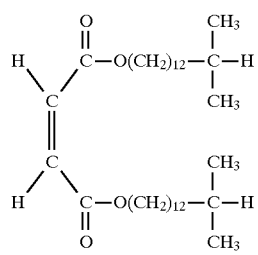

Di-isocetyl Maleate.

C.

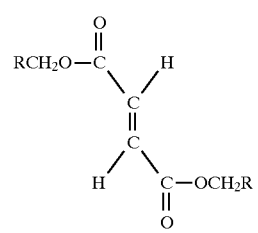

($C_{12}$–$C_{15}$) alcohol blend Fumarate

D.

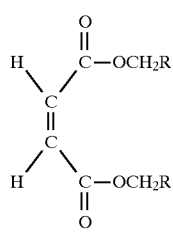

($C_{12}$–$C_{15}$) alcohol blend Maleate where R is a blend of ($C_{11}$–$C_{14}$) straight chain alkyl groups.

Following is a chart which gives a summary of the Safety Tests of the preferred embodiment of the invention:

| ESTERS | DRAIZE DERMAL | DRAIZE OCULAR | FHSA ORAL |
|---|---|---|---|
| Di isocetyl Fumarate (solvent method) | 0 | 0 | 0 |
| Di isocetyl Fumarate (heat method) | 0 | 0 | N/A |
| Di isocetyl Maleate | 0 | 0 | N/A |
| ($C_{12}$–$C_{15}$) Alcohol Fumarate (Solid-M.P. 36–37 C) | 0 | 0 | 0 |
| ($C_{12}$–$C_{15}$) Alcohol Maleate (liquid) | 0 | 0 | 0 |

The diisocetyl fumarate when applied "neat", gives silky oiliness after 5 minutes. Initially, it feels "Sebum" like, but after 60 seconds it becomes dry, oily and, finally, silky. This is a desirable property because of its unusual emolliency characteristics. This ester has a low freezing point, pigment wetting properties, emulsifies readily, unusual safety and excellent stability.

The $C_{12}$–$C_{15}$ blended alcohols fumarate exhibits another unusual property which is unique. It is a solid with melting point at body temperature (36°–37° C.) which makes it a unique product for use in cosmetic formulations, e.g., lipstick.

The $C_{12}$–$C_{15}$ blended alcohols fumarate and maleate exhibit excellent color, odor and stability after six months at 25° C. They are both binders and good wetters.

The $C_{12}$–$C_{15}$ fumarate is a solid which melts at body temperature which is an ideal physical property for the cosmetic chemist.

The $C_{12}$–$C_{15}$ maleate is a liquid with the unique properties previously described.

Following are various methods of producing diisocetyl fumarate and maleate along with test results obtained. These fumarate and maleate along with test results obtained. These fumarate and maleates may be made either by the solvent method, that is, using azeotropic toluene and water as a solvent or the steam heat (solvent free method).

Following are sample formulations using the instant invention (Marrix).

FOUNDATION LOTION P-5-4-1

| PHASE A: Mix and dissolve at 20° C. | Hetester PHA | 10.0 |
|---|---|---|
| | Marrix | 10.0 |
| | Parsol MCX | 3.0 |
| | Isostearic Acid | 3.0 |
| | Isocetyl Alcohol | 1.0 |
| | Triethanolamine (99%) | 1.0 |
| PHASE $B_1$: disperse 20° C. | Water, Dironized | 59.6 |
| PHASE $B_2$: (dry blend) | Veegum | 0.7 |
| | Keltrol | 0.3 |
| PHASE C: | Pulverized Pigment Blend | 10.0 |
| | Cabosil M-5 | 1.3 |
| PHASE D: | Kathon CG | 0.1 |
| | | 100.0% Total |

PROCEDURE: Add $B_2$ to $B_3$—dispense until uniform—then add Phase "A"—mix 10 minutes—then add Phase "C"—mix 15 minutes—then add Phase "D". Mix all for 10 more minutes.

Hetester PHA—Propylene glycol isocetheth—20 acetate

Marrix—Fumaric and Maleic acid esters $C_{12}$–$C_{26}$ alcohols

Parol MCX—Octyl Methoxy Cinnamate

Veegum—Magnesium Aluminum Silicate

Keltrol—Xanthan Gum

Cabosil M-5—Fumed Silica

Kathon CG—Preservative

LIPSTICK

PHASE A—WAX BASE

| Marrix | 60.3 |
|---|---|
| (2) Ozakerite 170 | 7.0 |
| (2) White Beeswax | 6.0 |
| (2) Carnuba Wax | 1.5 |

-continued

|   |   |
|---|---|
| (2) Candelilla Wax | 1.5 |
| (2) Paraffin 143/145 | 1.5 |

PHASE B—COOR MIX

|   |   |
|---|---|
| (3) Titanium Dioxide 328–55% in Castor Oil | 6.3 |
| (4) Red #6 C19022-30% in Castor Oil | 3.2 |
| (4) Yellow #6-C705270 30% in Castor Oil | 1.4 |
| (5) Red #7-T429R | 2.4 |
| (5) Blue #1-T427BL | 0.8 |
| (5) Yellow #5-T428Y | 8.1 |
|   | 100.0% |

PROCEDURE:

Weigh and combine the ingredients of Phase "A". Heat to 85° C. and mix until uniform. Combine Phase "B" and slowly add color mix to the melted wax base. Mix all together at 85° C. until uniform. Cool to 70° C. and mold.

SUPPLIERS:

(2) Frank B. Ross Company, Inc.
(3) Whittaker, Clark & Daniels, Inc.
(4) Sun Chemical Corp. Pigment Division
(5) Crompton & Knowles, Inc.
(n) Note: This lipstick can be made totally castor oil free by grinding the pigment of Phase "B" in Marrix.

EMOLLIENT LOTION F-5-3-1

|   |   |   |
|---|---|---|
| PHASE A: | Water, dironized-30° C. | 78.7 |
| PHASE B: | Veegum | 0.8 |
| (dry blend) | Keltrol | 0.4 |
| PHASE C: | Hetester PCA 25° C. | 10.0 |
| (mix) | Marrix | 10.0 |
| PHASE D: | Kathon CG | 0.1 |
| PHASE E: | Fragrance | O.S. |
|   |   | 100% Total |

PROCEDURE: Add Phase "B" to Phase "A" and dispense until uniform—then add Phase "C"—Mix until uniform—then add Phase "D", then Phase "E"—mix 15 minutes Veegum—Magnesium Aluminum Silicate
Keltrol—Xanthan Gum
Hetester PCA—Propylene Glycol Ceteth 3 Acetate
Marrix—Fumaric and Maleic acid esters of $C_{12}$–$C_{26}$ alcohols
Kathon CG—Preservatives

DRY SKIN LOTION

|   |   |
|---|---|
| PHASE A (45° C.): |   |
| Water, deionized | 58.25 |
| PHASE B (45° C.) (Disperse First): |   |
| Hetester ® PHA | 9.00 |
| (1) Pemulen ® TR-2 | 0.30 |
| Then add remaining ingredients of Phase B: |   |
| Elefac ® I-205 | 4.50 |
| Marrix ® SF | 4.50 |
| CUPL ® PIC (40° C.) | 2.00 |
| (2) Dow Corning Volatile Silicone 344 | 9.00 |

-continued

|   |   |
|---|---|
| PHASE C. (Dissolve) |   |
| Water, deionized | 1.26 |
| Triethanoiamine-99% | 0.24 |
| PHASE D: (Disperse) |   |
| Water, deionized | 9.80 |
| (3) Keltrol ® | 0.10 |
| PHASE E: |   |
| (4) Germaben ® IIE | 1.00 |
| PHASE F: |   |
| Disodium EDTA | 0.05 |
|   | 100.00% TOTAL |

PROCEDURE: Add entire Phase B to Phase A; mix well; next add Phase C and mix. Add Phases D, E and F—mixing after each addition. Cool to 30°.

DI ISOCETYL FUMARATE

|   | # moles | wt. charged |
|---|---|---|
| C. W. Isocetyl Alcohol 244 | 2.00 | 488 |
| Fumaric Acid 116 | 1.05 | 122 |
| Catalyst Charge |   |   |
| p-Toluene Sulfonic Acid |   | 2.3 |
| Phosphorous Acid |   | 0.5 |
| Solvent |   |   |
| Toluene |   | 100 |
| Water to be Recovered: |   |   |
| 36 |   |   |

Procedure:

Heat all of the above materials under reflux using a water trap to collect water of esterification. Water starts coming over at 120° C. and continues to about 151° C. This takes about 6–8 hours depending upon the batch size. When all the water has been removed (36), the heat is removed and the batch cooled to room temperature.

Washing Procedure

The crude is charged into a separatory funnel along with an equal volume of 5% salt solution. The salt solution should be 40°–50° C. in order to speed separation. This wash removes most of the catalyst and unreacted fumaric acid.

A second wash is composed of an equal volume of water containing 5% salt and 5% sodium carbonate also at 40°–50° C. After mixing well, a milk like-emulsion is obtained which will separate after standing for a time. The separation is difficult to see because both oil phase and water phase are milk like but the phases can be seen upon close observation. The crude is washed twice more with an equal volume of 5% salt solution at 40°–50° C. These separations are not difficult to see.

The bulk of the toluene is removed at 80° C. under 50 mm. vacuum. The remaining traces of solvent is removed at 130° C. and 10 mm. vacuum. The salt solids are then filtered off to finish the batch.

Process Notes

1. Phosphrous acid is added to p-toluene sulfonic acid to help preserve color during reaction.

2. The total amount of recovered water is less then theory because of the solubility of it in toluene.

3. Using warm (40°–50° C.) 5% salt solution speeds the rate of separation of the oil phase.

4. Removing the bulk of toluene at 50–55 mm. and 80° C. helps maintain good color.

5. It is necessary to use a higher vacuum and temperature in order to remove the last traces of solvent odor.

6. Fumaric acid used in this work came from Monsanto and Fluka GG. Alcohols are manufactured by Exxon and are part of their Exxal series.

Analysis of Product

A. V.=0.05
S. V.=184.3
OH=12.6

Preparation of Esters From Some of The Other Exxal Alcohols (1) Exxal 18 (Isostearyl Alcohol)
  OH=202
  C.W.=278
(2) Exxal 20 (Isoarachidyl Alcohol)
  OH=188
  C.W.=289
(3) Exxal 26 (flexicosyl Alcohol)
  OH=130
  C. W.=431.5

Exxal 18 and 20 reacted the same as the isocetyl compound. On the other hand, Exxal 26 would not react with the Fumaric acid under any of the catalyst systems tried.

In order to obtain the Exxal 18 and 20 esters, the weight of alcohol must be changed. In place of 488 isocetyl use 566 of isostearyl and 597 of isonrachidyl alcohol.

Analysis:
Isostearyl Ester
A.V.=0.22
S.V.=160.1
OH=10.8
Isoarachidyl Ester
A.V.=0.33
S.V.=149.7
OH=10.7

WATER WASHING PROCEDURE

Washing of all these esters requires care because it is difficult to see the phase separation. Both the oil phase and the water phase contain suspended solids. If this operation is not watched carefully losses of as much as 30% of the yield could be experienced.

Procedure:

(1) Determine the acid value of the finished batch. This is done when the theoretical amount of water of esterification is obtained. This amount may not always be recovered because a certain amount remains in the equipment. A better way to monitor the batch is to start checking the acid value of the batch as the amount of water reaches the theoretical value. When the acid value remains constant for about an hour it has probably reached completion. The water should be close to theory. Check the final acid value. This will be used to calculate the necessary amount of caustic to add to neutralize the free acid. In the lab 0.1% excess sodium hydroxide is used. The resulting crude can be cooled to about 30°–40° C. by the addition of about one third its volume of cold water. When this has been added, with good agitation, add the necessary sodium hydroxide as a 50% solution along with enough salt to form a 5% solution. After mixing for a time, 10–20 minutes in the lab, the pH can be checked with pH paper. The pH should be between 8–9. If the batch is still acid to pH paper, run an acid value and calculate the amount of sodium hydroxide required.

(2) After the necessary pH requirements have been made, the mixture is heated to 70° C. with good agitation. Stop agitation and allow the phases to separate. The water layer will be quite clear and the separation easily made. The oil phase will contain white solids along with water. Remove water phase.

(3) Repeat this washing procedure with the same amount of water and salt. Heat as above. Repeat as necessary until the wash water has the same pH as the starting water.

(4) When phases have been separated, heat the batch to 100° C. and 55 mm vacuum until all water has been removed. The resulting oil will have solids suspended in it.

(5) The resulting oil can be filtered warm if necessary at 70° C. max. A good grade of fine dry filter cell should be used.

Conclusions:

The use of a larger volume of water along with salt and a 70° C. heating makes separation easy. Recoveries of better then 90% are achieved in the lab.

DIISOCETYL FUMARATE (solvent free method)

In order to determine the proper mole ratio of fumaric acid to Exxal 16, the following three reactions were run.

Reaction 11
1 mole fumaric acid
2 moles Exxal 16

In all reactions both p-toluene sulfonic acid and hypophosphorous acid were used. The latter material is used to prevent color formation and eliminate the need for carbon treatment.

Analysis:
  A.V.=0.3
  S.U.=186.3
  O.H.=8.64

Reaction #2
0.95 mole fumaric acid
2.b moles Exxal 16
Analysis:
  A.V.=0.11
  S.U.=171.9
  O.H.=27.3

Reaction 13
1.05 moles fumaric acid
2.0 moles Exxal 16
Analysis:
  A.V.=0.08
  S.U.=190.8
  O.H.=8.7

It can be seen that the ratio used in reaction #3 gives the greatest amount of ester.

Based on these results the following batches were prepared.

DIISOCETYL FUMARATE (SOLVENT FREE)

| fumaric acid | 122.0 g | (1.05) |
| Exxal 16 | 500.0 g | (2.0 ) |
| p-toluenesulfonic acid | 1.4 g | 0.2% |
| hypophosphoric acid | 1.4 g | 0.2% |

The above materials are heated slowly to 130°–155° C. under a nitrogen sparge. There is some initial foaming which is controlled by the rate of addition and the rate of agitation. After about half of the water is removed, foaming is no longer a problem.

| | |
|---|---|
| Water removed: | 32 g |
| A. V. of crude | 15.9 |

A second identical batch was prepared using the same quantities.

| | |
|---|---|
| Water removed: | 33 g |
| A.V. of crude | 10 |

Both batches were combined and neutralized with the required amount of sodium hydroxide.
Addition of caustic produces a thick emulsion which requires the addition of salt to separate. This separation is very difficult to see. Care it required. Each wash results in the same problem and salt is required even when the oil is neutral there are still solids suspended in the oil phase. this neutralized product containing the solids is dried at 100° C. and 55 mm until all the water has been removed. The resulting product is cooled to room temperature and filtered.
Analysis:
A.V.=0.5
O.H.=5.56
S.U.=184.8

DIISOCETYL FUMARATE (toluene method)

Two batches were prepared using the method described in the first report.
Analysis:
A.V.=0.26
O.H.=12.8
S.U.=180.5
It can be seen that the ratio used in reaction #3 gives the greatest amount of ester.

DI NEODOL 25 FUMARATE

| | | | |
|---|---|---|---|
| Fumaric Acid | 116.0 × 1.05 | = | 122.0 g |
| C.W. = 116 | | | |
| Neodol 25 | 202.5 × 2 | = | 405.0 g |
| C.W. = 202.5 | | | |
| p-Toluenesulfonic Acid | 0.2% | | 1.0 g |
| Hypophosphoric Acid | 0.2% | | 1.0 g |
| $N_2$ Sparge | | | |

Above materials are heated with good agitation. Water starts distilling out at 80° C. to 90° C. Remaining water comes over between 128° C. and 146° C. Recovered water equals 35 g out of 36 g.

| | |
|---|---|
| Crude Yield | 533.0 g |
| A.V. 19.9 | |
| Weight required to neutralize free acid: | |
| Na OH | 10.7 g |

Use standard washing procedure.

DI ISOCETYL FUMARATE ex. EUTANOL G 16

| | | | |
|---|---|---|---|
| Fumaric Acid | 116.0 × 1.05 | = | 122.0 g |
| C.W. = 116 | | | |
| Neodol 25 | 267 × 2 | = | 534.0 g |
| C.W. = 267 | | | |
| p-Toluenesulfonic Acid | 0.2% | | 1.3 g |
| Hypophosphoric Acid | 0.2% | | 1.3 g |
| $N_2$ Sparge | | | |

Above materials are heated with good agitation. Water starts distilling out at 134° C. and continues until 180° C. A total of 31 g of water was recovered.
Crude ester contained suspended solids which were removed by filtration.
A. V.=1 11.5

| | |
|---|---|
| Crude Yield | 585.0 g |
| (should be about 600–610 g but product lost in filtration). | |
| Weight required to neutralize free acid: | 7.0 g |
| Na OH | |

Use standard washing procedure.

DI ISOCETYL MALEATE

| | | | |
|---|---|---|---|
| Maleic Anhydride | 98 × 1.05 | = | 103.0 g |
| C.W. = 98 | | | |
| Exxal 16 | 250 × 2 | = | 500.0 g |
| C.W. = 250 | | | |
| p-Toluenesulfonic Acid | 0.25% | | 1.5 g |
| Hypophosphoric Acid | 0.25% | | 1.5 g |
| $N_2$ Sparge | | | |

Above materials are heated with good agitation. Water starts distilling at 95° C. to 100° C. and continues until 170° C. is reached. About 14 ml of water is collected in the trap. Some solids sublime into the trap and some remain in trap.

| | |
|---|---|
| Crude Yield | 585.0 g |
| A.V. = 19.2 | |
| Weight required to neutralize free acid: | 12.0 g |
| Na OH | |

Use standard washing procedure.

DI ISOCETYL HALEATE TOLUENE AZEOTROPE

| | | | |
|---|---|---|---|
| Maleic Anhydride | 98 × 1.05 | = | 103.0 g |
| C.W. = 98 | | | |
| Exxal 16 | 250 × 2 | = | 500.0 g |
| C.W. = 250 | | | |
| Toluene | | | 100.0 g |
| p-Toluenesulfonic Acid | 0.25% | | 1.4 g |
| Hypophosphoric Acid | 0.25% | | 1.4 g |

Above materials are heated with good agitation. Azeotrope starts at 118° C. Temperature increases to 170° C. as the reaction progresses. A total of 19 g water and 71 ml toluene was recovered.

| | |
|---|---|
| Crude Yield | 633.4 g |
| A.V. = 6.8 | |
| Weight required to neutralize free acid: | 4.4 g |
| Na OH | |

Using standard washing procedure.

DI ISOCETYL FUMARATE ex. EUTANOL G 16 AND TOLUENE

| | | | |
|---|---|---|---|
| Fumaric Acid | 116.0 × 1.05 | = | 122.0 g |
| C.W. = 116 | | | |
| Eutanol G 16 | 267 × 2 | = | 534.0 g |
| C.W. = 267 | | | |
| Toluene | | | 150.0 g |
| p-Toluene Sulfonic Acid | 0.2% | | 1.3 g |
| Hypophosphoric Acid | 0.2% | | 1.3 g |

Above materials are heated with good agitation. Azeotrope starts at 125° C. and continues up to 168° C. where 35 ml of water is recovered.

| | |
|---|---|
| Crude Yield | 760.0 g |
| A.V. = 14 | |
| Weight required to neutralize free acid: | |
| Na OH | 10.6 g |

Use standard washing procedure.

What is claimed is:

1. An emollient composition consisting essentially of compounds of the structure:

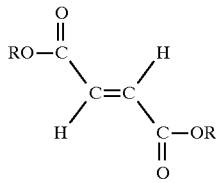

where R is a blend of $C_{12}$–$C_{15}$ straight chain alkyl groups and wherein said composition is a solid at room temperature and melts at body temperature.

2. The emollient composition according to claim 1 wherein said blend is obtained from a mixture of $C_{12}$–$C_{15}$ straight chain alcohols, said mixture comprising 27 to 35% by weight of a $C_{12}$ alcohol, 30 to 38% by weight of a $C_{13}$ alcohol, 14 to 22% by weight of a $C_{14}$ alcohol and 13 to 20% by weight of a $C_{15}$ alcohol.

3. An emollient composition consisting essentially of the reaction product of fumaric acid and a blend of $C_{12}$–C15 straight chain alcohols wherein said composition is a solid at room temperature and melts at body temperature.

4. The emollient composition according to claim 1 wherein said blend of alcohols comprises 27 to 35% by weight of a $C_{12}$ alcohol, 30 to 38% by weight of a $C_{13}$ alcohol, 14 to 22% by weight of a $C_{14}$ alcohol and 13 to 20% by weight of a $C_{15}$ alcohol.

5. A lotion composition comprising an emulsifier, thickener, stabilizer, water and an emollient composition, said emollient composition comprising 4.5% to 10% by weight of said lotion composition, said emollient composition consisting essentially of compounds of the structure:

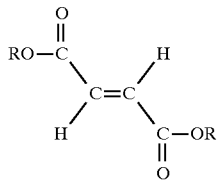

where R is a blend of $C_{12}$–C15 straight chain alkyl groups and wherein said emollient composition is a solid at room temperature and melts at body temperature.

6. The lotion composition according to claim 5 wherein said blend is obtained from a mixture of $C_{12}$–C15 alcohols which comprises 27 to 35% by weight of a $C_{12}$ alcohol, 30 to 38 % by weight of a $C_{13}$ alcohol, 14 to 22% by weight of a C14 alcohol and 13 to 20% by weight of a $C_{15}$ alcohol.

7. The composition according to claim 5 wherein said emulsifier is propyleneglycol isoceteth-3-acetate, said thickener is selected from the group consisting of xanthan gum and mixtures of xanthan gum, aluminum silicate and fumed silica, said composition further comprising octyl methoxy cinnamate.

8. A lipstick composition comprising wax, a pigment dispersion and an emollient composition, said emollient composition comprising 60.3% by weight of said lipstick composition, said emollient composition consisting essentially of compounds of the structure:

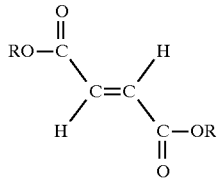

where R is a blend of $C_{12}$–$C_{15}$ straight chain alkyl groups and wherein said emollient composition is a solid at room temperature and melts at body temperature.

9. The lipstick composition according to claim 7 wherein said blend is obtained from a mixture of $C_{12}$–$C_{15}$ alcohols which comprises 27 to 35% by weight of a $C_{12}$ alcohol, 30 to 38% by weight of a $C_{13}$ alcohol, 14 to 22% by weight of a $C_{14}$ alcohol and 13 to 20% by weight of a $C_{15}$ alcohol.

10. The composition according to claim 8 wherein said wax is a mixture of ozokerite, beeswax, carnauba wax, candellila wax and paraffin and said pigment dispersion contains a mixtures of pigments dispersed in castor oil.

\* \* \* \* \*